(12) United States Patent
Blease et al.

(10) Patent No.: US 8,673,816 B2
(45) Date of Patent: Mar. 18, 2014

(54) SURFACTANTS IN AGROCHEMICAL FORMULATIONS

(75) Inventors: Trevor Graham Blease, Stockton-on-Tees (GB); Gregory James Lindner, Wilmington, DE (US); Lee David Richards, Newark, DE (US)

(73) Assignees: Croda, Inc., Edison, NJ (US); Croda International PLC, Goole, East Yorkshire (GB)

( * ) Notice: Subject to any disclaimer, the term of this patent is extended or adjusted under 35 U.S.C. 154(b) by 0 days.

(21) Appl. No.: 13/266,873

(22) PCT Filed: May 5, 2010

(86) PCT No.: PCT/US2010/033708
§ 371 (c)(1),
(2), (4) Date: Oct. 28, 2011

(87) PCT Pub. No.: WO2010/129662
PCT Pub. Date: Nov. 11, 2010

(65) Prior Publication Data
US 2012/0040834 A1    Feb. 16, 2012

Related U.S. Application Data

(60) Provisional application No. 61/213,126, filed on May 8, 2009, provisional application No. 61/282,125, filed on Dec. 18, 2009.

(51) Int. Cl.
| | |
|---|---|
| *A01N 25/00* | (2006.01) |
| *A01P 7/02* | (2006.01) |
| *C07C 217/04* | (2006.01) |
| *A01P 21/00* | (2006.01) |
| *A01N 57/20* | (2006.01) |
| *A01N 25/04* | (2006.01) |
| *A01P 13/00* | (2006.01) |
| *A01P 7/04* | (2006.01) |

(52) U.S. Cl.
USPC ........... 504/206; 554/109; 514/785; 504/362; 71/64.08

(58) Field of Classification Search
USPC ......................................................... 504/206
See application file for complete search history.

(56) References Cited

U.S. PATENT DOCUMENTS

| | | | |
|---|---|---|---|
| 2,247,402 A | 7/1941 | Perkins et al. | |
| 5,078,782 A * | 1/1992 | Nielsen et al. | ................ 504/135 |

FOREIGN PATENT DOCUMENTS

| | | | |
|---|---|---|---|
| EP | 0633057 | 1/1995 | |
| WO | WO 96/16930 | 6/1996 | |
| WO | WO 00/35863 | 6/2000 | |
| WO | WO00/35863 | * 6/2000 | .................. 504/206 |
| WO | WO 01/05224 | 1/2001 | |
| WO | WO 03/067983 | 8/2003 | |
| WO | WO 03/106010 | 12/2003 | |
| WO | WO 2004/112478 | 12/2004 | |

OTHER PUBLICATIONS

International Search Report dated Aug. 19, 2010 for PCT/US2010/033708.

* cited by examiner

*Primary Examiner* — Janet Epps-Smith
*Assistant Examiner* — Audrea Buckley
(74) *Attorney, Agent, or Firm* — Jones Day

(57) ABSTRACT

Surfactant compounds which include an amine ended polyalkylene glycol hydrophile linked to $C_{22}$ to $C_{60}$ mainly hydrocarbyl, particularly composite hydrocarbyl, especially derived from a polymerised fatty acid and/or an aralkyl substituted phenol, hydrophobe, are useful in dispersing solids, particularly active agrochemicals, in aqueous media, or as adjuvants in agrochemical formulations, particularly of water soluble non-selective herbicides. In particular the hydrophobe is derived from polymerised fatty acids, such as dimer and, especially, trimer acids or from aralkyl substituted phenols. Aqueous dispersions using such surfactants can remain stable even with substantial concentrations of electrolyte e.g. in stable agrochemical dispersions including water soluble electrolyte agrochemical, such as glyphosate and/or ammonium sulphate.

37 Claims, No Drawings

SURFACTANTS IN AGROCHEMICAL FORMULATIONS

This application is the National Phase application of International Application No. PCT/US20101033708, filed May 5, 2010, which designates the United States and was published in English, which further claims the benefit of priority from U.S. Provisional Application No. 61/213,126, filed May 8, 2009, and U.S. Provisional Application No. 61/282,125, filed Dec. 18, 2009. The foregoing related applications, in their entirety, are incorporated herein by reference.

This invention relates to novel surfactants, in particular to amine group containing alkoxylated derivatives of polymerised fatty acids or aralkyl phenols and their use, particularly in agrochemical formulations as dispersants and/or adjuvants, especially in aqueous systems, to aqueous formulations, particularly dispersions made using the dispersants, and agrochemical formulations, particularly to agrochemical dispersion formulations including such dispersants and formulations containing the adjuvants, and to the treatment of crops using such agricultural formulations.

Surfactants are widely used in agrochemical compositions and formulations for various reasons including as adjuvants, dispersants, wetting agents, emulsifiers or solubilisers (and may serve more than one such function). Adjuvants act to increase the activity or effectiveness (by a variety of possible mechanisms) of an agrochemical in a formulation; dispersants are used to improve the stability and uniformity of dispersions of solid components in liquid media; wetting agents improve the wetting of agrochemical sprays on the target substrate, usually plant leaves; emulsifiers are used to emulsify liquid agrochemicals in aqueous media, to emulsify oils used as solvents or diluents for agrochemicals and/or to emulsify oils used as formulation additives (to provide improved properties); and solubilisers are used to improve the solubility or compatibility of otherwise insoluble/incompatible formulation components. The benefit of including surfactants in agrochemical formulations is widely recognised and is a very widespread practice.

Agrochemical dispersions including dispersants can be formulated as dispersion concentrates, which are a form of agrochemical concentrate formulation in which a water insoluble agrochemical is dispersed as solid particles in an aqueous continuous phase. This formulation type includes suspoemulsion formulations which include components in both a dispersed solid phase and in a dispersed liquid (emulsion) phase. It is usually necessary to include a dispersant in the concentrate to maintain the solid dispersed agrochemical (and any other dispersed solids) in suspension. Such concentrates are normally diluted to give a sprayable (dilute) formulation. The requirements for such dispersants are challenging as it is generally desirably to have a high proportion of suspended solids in the concentrate and the water insoluble agrochemicals are frequently hydrophobic and the dispersant may need to act effectively in the presence of other surfactant materials. Frequently it will be necessary to use dispersants with suitable hydrophobes and materials like Atlox 4913 (ex Croda), an acrylic ester/acrylic acid copolymer including PEG ester side chains, and Soprophor FLK and 4D-384 (ex Rhodia), respectively phosphate and sulphate esters of a tristyrylphenol ethoxylate, are used to provide the specific dispersancy required. EP 0633057 A of Rhone-Poulenc describes the use of tristyrylphenol ethoxylate type dispersants. Those skilled in the art will recognise that the compound tristyrylphenol may be more systematically described as tris[1-(phenyl)ethyl]phenol or 2,4,6-tris[1-(phenyl)ethyl]phenol and correspondingly the tristyrylphenyl group (tristyrylphenol less the phenolic OH group). However, "tristyrylphenol" and "tristyrylphenyl" are convenient and concise and are generally used herein.

Even such high performance dispersants are not perfect, and one feature they lack is dispersion stability in high ionic strength media, in particular where another component of the formulation is a water soluble electrolyte e.g. in combination formulations including water soluble electrolyte herbicide such as bipyridyl herbicides or glyphosate.

The present invention is based on our finding that compounds having an amine ended polyalkylene glycol hydrophile and a relatively large, typically $C_{22}$ to $C_{60}$, mainly hydrocarbyl, particularly composite hydrocarbyl, typically including branched and/or cyclic groups or constituents, hydrophobe can be effective adjuvants and/or very effective dispersants for water insoluble agrochemicals in aqueous dispersions, particularly such dispersions which also include substantial concentrations of electrolyte.

Accordingly the present invention provides a surfactant which is a compound comprising an amine ended polyalkylene glycol hydrophile(s) linked to a $C_{22}$ to $C_{60}$ mainly hydrocarbyl hydrophobe.

Particular compounds of the invention are those of the formula (I). The compounds of and used as dispersants in the invention can be of the general formula (I):

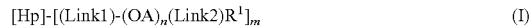

$$[Hp]\text{-}[(Link1)\text{-}(OA)_n(Link2)R^1]_m \qquad (I)$$

where

Hp is a $C_{22}$ to $C_{60}$ mainly hydrocarbyl hydrophobe;

Link1 is a linking group, particularly a direct bond, —CO—, an oxycarboxylic acid group —OR⁸C(O)— where R⁸ is a $C_1$ to $C_4$ alkylene group, or a dicarboxylic acid group —OC(O)R⁹C(O)— where R⁹ is a $C_2$ to $C_4$ alkylene group, or a carbonate group —OC(O)—;

OA is a oxyalkylene residue, particularly an oxyethylene or oxypropylene residue, and may vary along the chain;

n is from 5 to 50, more usually from 8 to 25, particularly from 10 to 15;

Link2 is a linking group, particularly a direct bond, a group —OCH₂CH(CH₃)—, a group —OCH₂CH(OH)CH₂—, a dicarboxylic acid derived group —OC(O)R¹⁰C(O)(X)(CH₂)$_{n1}$— where R¹⁰ is a C2 to C4 alkylene group and n1 is from 2 to 6, a group —CH₂C(O)(X)(CH₂)$_{n2}$—, where X is —O— or —NH— and n2 is from 2 to 6;

R¹ is a group —NR²R³ where R² and R³ each independently represent hydrogen, alkyl, particularly $C_1$ to $C_8$ alkyl, alkenyl, particularly $C_2$ to $C_8$ alkenyl, or together with the nitrogen atom carrying them form a heterocyclic, particularly a 5 to 7 membered ring, that may include one or more further heterocyclic atoms; a group —(R⁴)(R⁵)N→O; a group —(R⁴)(R⁵)N⁺—R⁶; or a group —(R⁴)(R⁵)N⁺—R⁷.COO⁻, where R⁴ and R⁵ each independently represent alkyl, particularly $C_1$ to $C_8$ alkyl, alkenyl, particularly $C_2$ to $C_8$ alkenyl, or together with the nitrogen atom carrying them form a heterocyclic, particularly a 5 to 7 membered ring, that may include one or more further heterocyclic atoms; R⁶ is alkyl, particularly $C_1$ to $C_6$ alkyl; and R⁷ is alkylene, particularly $C_1$ to $C_5$ alkylene, more particularly a —CH₂— group.

In particular in the compounds of the invention, the hydrophobe is derived from a polymerised fatty acid and/or an aralkyl substituted phenol.

The compounds of and used in this invention are described as being "amine ended" referring to the compounds having an amine group at one end of the oxyalkylene chain hydrophile in the molecule (possibly with a linking group—see below—between the amino function and the oxyalkylene chain of the hydrophile). The amine group may be a primary, secondary, tertiary or quaternary amino group or a tertiary amine N-oxide group, but is particularly a tertiary amine or tertiary amine N-oxide group or quaternary amino, including betaine, group.

The compounds of the invention have particular utility as dispersants and/or adjuvants in agrochemical formulations. The invention accordingly includes:

i) an agrochemical dispersion, in the form of an agrochemical concentrate or a diluted agrochemical spray formulation, particularly a dispersion concentrate, of a solid, particularly a solid active agrochemical, in an aqueous liquid, particularly an aqueous concentrate including also dissolved electrolyte, which includes as a dispersing agent, one or more compounds of the invention, particularly of the formula (I) above, particularly a compound of the formula (I) which has a composite hydrocarbyl hydrophobe, more particularly a hydrophobe including branched and/or cyclic groups or constituents;

ii) an agrochemical dispersion, in the form of an agrochemical concentrate or a diluted agrochemical spray formulation, particularly a dispersion concentrate, which includes water soluble electrolyte, particularly water soluble electrolyte agrochemical active, which includes as a dispersing agent, one or more compounds of the invention, particularly of the formula (I) above, particularly a compound of the formula (I) which has a composite hydrocarbyl hydrophobe, more particularly a hydrophobe including branched and/or cyclic groups or constituents;

iii) the use of a compound of the invention as a dispersant in an agrochemical dispersion formulation, particularly an agrochemical concentrate or an agrochemical diluted spray formulation, which formulation comprises an active agrochemical, particularly such a formulation including dissolved electrolyte;

iv) an agrochemical formulation, in the form of an agrochemical concentrate or a diluted agrochemical spray formulation, which comprises an active agrochemical, particularly at least one plant growth regulator, at least one pesticide and/or at least one herbicide, which includes, as an adjuvant, a compound of the invention, particularly of the formula (I) above, particularly a compound of the formula (I) which has a composite hydrocarbyl hydrophobe, more particularly a hydrophobe including branched and/or cyclic groups or constituents;

v) the use of a compound of the invention as an agrochemical adjuvant, particularly in an agrochemical formulation, particularly an agrochemical concentrate or an agrochemical diluted spray formulation, which formulation comprises an active agrochemical, particularly a water soluble pesticide or herbicide;

vi) an agrochemical formulation, in the form of an oil dispersion concentrate comprising a liquid phase of a water immiscible liquid, desirably an oil, a water insoluble agrochemical active present as finely divided and dispersed solid particles and including one or more compounds of the invention, particularly of the formula (I) above, particularly a compound of the formula (I) which has a composite hydrocarbyl hydrophobe, more particularly a hydrophobe including branched and/or cyclic groups or constituents;

vii) the use of a compound of the invention in oil dispersion concentrate agrochemical formulations;

viii) an agrochemical spray formulation which is a concentrate of any of aspects i), ii), iv) or vi) or a concentrate as used in use iii), v) or vii) above diluted with from 100 to 10000 times the weight of the concentrate of water;

ix) a method of treating vegetation by applying to plants and/or soil, particularly the soil adjacent to plants, a diluted formulation as set out under viii) above.

In use the concentrates of the invention will typically be diluted with water prior to application to crops or the soil surrounding crop plants, typically by spraying. The invention accordingly further includes a diluted formulation which comprises a concentrate of the invention, particularly a concentrate containing an adjuvant of the invention or a dispersion concentrate of the invention, and especially a concentrate of the invention further including water soluble electrolyte, diluted with from 10 to 10,000 times the weight of the concentrate of water.

The concentrates of the invention are typically used to treat crops so the invention further includes a method of treating vegetation by applying to plants and/or soil a diluted formulation of the invention, particularly a diluted formulation including water soluble electrolyte, especially a diluted adjuvant concentrate of the invention or a diluted dispersion concentrate of the invention.

Another way in which the formulations, particularly dispersion formulations, of the invention may be used is to treat seeds and the invention accordingly includes a method of treating seeds which comprises applying to the seeds a formulation, particularly a dispersion formulation, of the invention.

In the compounds of the invention, particularly of the formula (I), the hydrophobe, the residue Hp in formula (I), is a mainly hydrocarbyl $C_{22}$ to $C_{60}$ group. Desirably the hydrophobe is composite in that it is built up of smaller units, and usually includes branched and/or cyclic groups or constituents. A composite hydrophobe may be built of smaller units by polymerisation, or by a synthesis which substitutes onto a core fragment of the product molecule. Examples of polymerised composite hydrophobe groups are the residues of polymerised fatty acids which are commercially available as dimers, trimers, or (usually) mixtures of dimers with trimers, with mixtures that are trimer rich being particularly useful. Examples of hydrophobe groups that are synthesised by substitution on a core fragment include aralkyl substituted phenyl groups (usually as residues of the corresponding phenol), in particular di- and tri-(aralkyl) substituted phenyl groups. The resulting hydrophobes are di- and/or tri-(aralkyl)phenyl groups, particularly di- and/or tri-styryl or di- and/or tri-cumyl phenyl groups. Polymerised fatty acid residues are hydrocarbyl groups apart from the attached carboxyl groups (usually 1 or 2 per molecule apart from the carboxyl group providing or forming part of the link to the hydrophilic oxyalkylene chain). As is noted below, the polymerisation reaction gives a mixture of compounds, mainly having highly branched chain and usually including compounds having carbocyclic and sometimes aromatic rings. Di- and tri-(aralkyl) substituted phenyl groups are hydrocarbyl groups (the oxygen atom of the parent phenol forming part of the oxyalkylene chain) including multiple aromatic carbocyclic rings and are in effect branched (by virtue of the usually multiple aromatic ring substitution).

Accordingly the invention includes formulations, particularly a adjuvant containing formulation or a dispersion formulation of the invention, either as a concentrate and/or as a diluted formulation, particularly including water soluble electrolyte, especially water soluble electrolyte agrochemical actives e.g. glyphosate and/or Paraquat, and to the treatment, particularly by spraying of crops using such especially diluted formulations, where the adjuvant(s) and/or dispersant(s) of the invention, as appropriate, have a hydrophobe derived from polymerised fatty acid or (aralkyl) substituted phenol.

These two classes of hydrophobe will generally utilise different linking groups and the invention accordingly includes the corresponding compounds. Where the hydrophobe is derived from polymerised fatty acid the compounds of the formula (I) are of the formula (Ia):

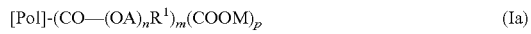

(Ia)

where

Pol is the residue of a polymerised fatty acid dimer or trimer apart from the carboxylic acid groups;

m is 1 (where Pol is the residue of a fatty acid dimer) or 1 or 2, and desirably 1, (where Pol is the residue of a fatty acid trimer);

p is 1 (where Pol is the residue of a fatty acid dimer) or 1, or 2, and desirably 2, (where Pol is the residue of a fatty acid trimer);

M is a hydrogen atom, a cationic salt forming species, particularly an alkali metal atom or an amine (including quaternary amine) or ammonium group; and OA, n and R1 are independently as defined for formula (I) above.

Where the hydrophobe is derived from an aralkylphenol the compounds of the formula (I) are typically of the formula (Ib):

(Ib)

where

ASP is an aralkyl phenyl group, particularly a di- or tri-(aralkyl)phenyl group;

Link1b is a direct bond, an oxycarboxylic acid group —OR$^8$C(O)—, where R$^8$ is C$_1$ to C$_4$ alkylene, a dicarboxylic acid derived group —OC(O)R$^9$C(O)—, where R$^9$ is C$_2$ to C$_4$ alkylene, or a carbonate group —OC(O)—;

Link2b is a direct bond, a group —OCH$_2$CH(CH$_3$)—, a group —CH$_2$CH(OH)CH$_2$—, a dicarboxylic acid derived group —C(O)R$^9$C(O)(X$^1$)(CH$_2$)$_{n1}$—, where R$^9$ is a C2 to C4 alkylene group, n1 is from 2 to 6 and where X$^1$ is —O— or —NH—, a group —CH$_2$C(O)(X$^2$)(CH$_2$)$_{n2}$—, where X$^2$ is —O— or —NH— and n2 is from 2 to 6;

OA, n and R$^1$ are independently as defined for formula (I) above.

The groups Link1 and Link2 in formulae (I), (Ia) and (Ib) link the hydrophobe and the polyalkoxylate chain and the polyalkoxylate chain and the terminal amino group respectively. Generally it is desirable that they are direct bonds or are as small as practical e.g. where the nominal linking groups forms part of the precursor molecule e.g. as in polymerised fatty acid hydrophobe precursors. However, the nature of the starting materials and/or the availability and/or convenience of suitable synthetic routes may dictate using more extended chemical groups as links.

In formula (Ia) Link1 is a group —CO— derived from the polymerised fatty acid (nominal) precursor (together with the oxyalkylene oxygen atom forming a linking carboxylic ester function); and Link2 is generally a direct bond (though notionally the oxyalkylene, generally oxyethylene, group nearest the terminal amino group could be regarded as a link group). In formula (Ib) Link1 is a direct bond (the oxyalkylene oxygen atom forming an ether linkage) an oxycarboxylic acid group —OR$^8$C(O)— where R$^8$ is C$_1$ to C$_4$ alkylene, a dicarboxylic group —OC(O)R$^8$C(O)—, or a carbonate group —OC(O)O—; and Link2' is a direct bond, a group —OCH$_2$CH(CH$_3$)—, a group —CH$_2$CH(OH)CH$_2$—, a dicarboxylic group —OC(O)R$^9$C(O)(X$^1$)(CH$_2$)$_{n1}$—, or a group —CH$_2$C(O)(X$^2$)(CH$_2$)$_{n2}$— where R$^8$, R$^9$, X$^1$ and X$^2$ are as defined for formulae (I), (Ia) or (Ib) above. In any particular case the particular linking groups used will depend on the synthetic route used to make the compound of the invention (see below on synthesis). Correspondingly, the hydrophobe group Hp in formula (I) is (COOM)$_p$[Pol] in formula (Ia) and [ASP] in formula (Ib) (setting aside linking groups).

The hydrophilic part of the molecule is the polyalkoxylate chain terminated [if appropriate including a linking group—Link2—in formula (I)] with an amino group [in formula (1) represented by the group R$^1$].

The group R$^1$ is an amino group and can be a, desirably tertiary, amino group —NR$^2$R$^3$; a tertiary amino amine oxide group —(R$^4$)(R$^5$)N→O; a quaternary amino group —(R$^4$)(R$^5$)N$^+$(R$^6$); or a quaternary betaine group —(R$^4$)(R$^5$)N$^+$—R$^7$.COO$^-$. In these possibilities the groups R$^2$, R$^3$, R$^4$ and R$^5$ each independently represent alkyl, particularly C$_1$ to C$_8$, more particularly C$_1$ to C$_6$, alkyl; alkenyl, particularly C$_2$ to C$_8$, more particularly C$_2$ to C$_6$, alkenyl; or together with the nitrogen atom carrying them form a heterocyclic, particularly a 5 to 7 member, ring which may include one or more further heterocyclic atoms, such as N-tetrahydropyrrolyl, N-piperidinyl, N-morpholinyl and N-piperazinyl, commonly with a lower alkyl e.g. C$_1$ to C$_4$, substituent on the other nitrogen atom as in N-(4,N-methyl-)piperazinyl; R$^2$ and R$^3$ may each also be hydrogen, though this is not particularly preferred; R$^6$ is alkyl, particularly C$_1$ to C$_6$ alkyl; and R$^7$ is C$_1$ to C$_5$ alkylene, particularly —CH$_2$—.

The oxyalkylene group OA are particularly oxyethylene or oxypropylene residues. Generally it is desirable for compatibility in aqueous systems, particularly in aqueous solution or dispersion, that the polyoxyalkylene oxide chain, —(OA)$_n$- is a homopolymeric polyoxyethylene chain. However, copolymeric chains including oxypropylene residues may be used if desired e.g. in compounds of the formula (Ia) as capping groups adjacent the carboxyl group to improve the hydrolytic stability of the ester products, or in compounds of the formula (Ib) the use of an oxypropylene group as Link2 could be viewed as including an oxypropylene group at the end of the polyoxyalkylene chain. When present the proportion of oxypropylene residues will typically be less than 50 mole %, usually less than 25 mole % and more usually less than 15 mole %. When mixtures of oxyethylene and oxypropylene units are present the co-polymeric chains can be random (stochastic) or block (including taper block) copolymer chains as well as the chain end possibilities mentioned above.

In the esters of the formula (I) of and used in the invention, the number, n, of oxyalkylene residues in the chain, within the broad range of 5 to 50, will usually be at least 7.5 and desirably at least 10. It is unlikely that chains much longer than about 25 will offer any substantial benefit in stabilising dispersions or in providing adjuvancy, so desirably n is not more than 20 and will usually be not more than 15. As those skilled in the art will readily appreciate the index n, being an average, may be non-integral.

The group "Link" in formula (I) links the hydrophobe and hydrophile in the compounds of and used in the invention. The type of link used will generally depend on the nature of the hydrophobe and thus the most appropriate synthetic routes to making the desired compound. In particular, where the hydrophobe is a polymerised fatty acid hydrophobe, Link is generally one of the fatty acid carboxyl functions i.e. a group —C(O)— esterified to the polyalkoxylate chain through the terminal oxygen atom of the normally hydroxy ended amine intermediate (see below on synthesis) and where the hydrophobe is an aralkylphenyl group, Link is generally a direct bond forming an ether link to the polyalkoxylate chain.

Where the hydrophobe is derived from polymerised fatty acids, particularly fatty acid dimer or more particularly trimer, the corresponding compounds used in this invention are polymerised fatty acid derivatives and the corresponding polymerised fatty acid will, in the free acid form, be of the formula (II):

[Pol]-(COOH)$_r$ (II)

where Pol is as defined above and r is 2 (where Pol is the residue of a fatty acid dimer) or 3 (where Pol is the residue of a fatty acid trimer).

Desirably, the compounds of the invention include a single group —(OA)$_n$R$^1$ i.e. m=1, with, correspondingly, p=1 (where Pol is the residue of a fatty acid dimer) or p=2 (where Pol is the residue of a fatty acid trimer) per molecule. Accordingly, particularly useful compounds are of the formulae (IIa) or (IIb):

[Pol$^d$]-(CO—(OA)$_n$R$^1$)(COOM) (IIa); and/or

[Pol$^t$]-(CO—(OA)$_n$R$^1$)(COOM)$_2$ (IIb)

where: each OA, R$^1$, M and n are independently as defined above, Pol$^d$ is the residue of a fatty acid dimer (apart from the carboxyl groups) and Pol$^t$ is the residue of a fatty acid trimer (apart from the carboxyl groups). Compounds of the formula (IIb), based on trimer acids, are particularly useful and effective as adjuvants and/or dispersants according to the invention.

Those compounds of and used in the invention that are based on fatty acid dimers and/or trimers include both amine and carboxyl functionality. In aqueous solution these compounds, whether or not carrying charge on a formal quaternary group, are likely to exist as zwitterions at least at moderate pH values. Although the formulae above may not explicitly set this out the zwitterion forms are included in the invention. Indeed it is our belief that zwitterions or the capability to form them, may contribute to the beneficial performance that we have observed in compounds of the invention, particularly as dispersants.

The polymerised fatty acid synthetic precursors of the compounds of the invention based on polymerised fatty acids, particularly of the formula (IIa) are fatty acid dimers or trimers, or a mixture containing both dimer and trimer. Polymerised fatty acids are well known materials that are usually made by thermal polymerisation of fatty acids, particularly unsaturated fatty acids such as oleic and/or linoleic acids, typically using an acidic catalyst. The reactions are complex, including carbon skeleton rearrangements, to give products including branched fatty acids and oligomers, particularly dimers and trimers of the fatty acids. The polymerised acids are often described as if they were mainly of the formula:

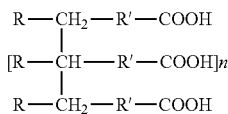

where each R is a typically C$_3$ to C$_{12}$, usually about C$_5$ to C$_{10}$, alkyl or alkenyl group; each R' is a typically C$_5$ to C$_{15}$, usually about C$_7$ to C$_{10}$, alkylene or alkeneylene group; and n is 0 or 1. However, this formula is at best only a rough guide as during polymerisation many reactions are possible including rearrangements which complicate the structures of the various groups and can give cyclic groups and linking groups between carboxylic acid chains rather than the simple bonds illustrated. Typically such polymerised fatty acids are manufactured industrially as mixtures of dimers and trimers commonly containing from 99 to 10% by weight dimer and correspondingly from 1 to 90% trimer. Nominal dimer and trimer products can be separated by distillation. In commercially produced product, for a nominal dimer the proportions will usually be from 99 to 60%, particularly 98 to 70%, dimer and 1 to 40%, particularly 2 to 30%, trimer and for a nominal trimer from 70 to 85%, particularly 75 to 80%, trimer and 30 to 15%, particularly 25 to 20%, dimer. Other mixtures can be made up by mixing nominal dimer and trimer products.

In principle the fatty acids used to make the dimer and/or trimer can be any unsaturated fatty acid, but more usually will be at least mainly C$_{10}$ to C$_{22}$ fatty acids, and usually at least mainly C$_{18}$ fatty acids, commonly oleic acid or mixtures of oleic and linoleic acids.

The polymerised acid residue may be unsaturated or saturated. As normally manufactured both dimer acids and trimer acids generally include at least some unsaturation and if desired this may be hydrogenated to produce the corresponding saturated materials. Generally fully saturated materials are more stable, particularly thermally and oxidatively stable than unsaturated materials. Of the polymerised fatty acids based on C$_{18}$ feedstocks, dimer acids generally have an average of 36 carbon atoms and trimer acids an average of 54 carbon atoms. The use of other feedstocks will give corresponding molecular weight dimer and trimer acids.

Aralkyl substituted phenyl group hydrophobes in the compounds of and used in this invention are particularly di- and/or tri-(aralkyl) substituted phenyl groups. In such groups the aralkyl substituent groups are typically phenyl substituted C$_2$ to C$_6$, more usually C$_2$ to C$_4$ and especially ethyl or propyl, particularly 2-propyl, alkyl groups. Examples of such aralkyl groups include styrylphenyl (1-pheneth-1-yl) groups, particularly di- and/or tri-styrylphenyl groups, or di- and/or tri-cumylphenyl (2-phenylprop-2-yl) groups. In these groups, the aralkyl substituent groups are usually in the 2, 4 and/or 6 positions on the phenyl group. Of these, tristyrylphenyl groups contain 30, distyrylphenyl groups 22, dicumylphenyl groups 24 and tricumylphenyl groups 33, carbon atoms respectively.

Aralkylphenyl groups can be provided to the compounds of and used in the invention using the corresponding phenols as starting materials. The aralkyl substituted phenols can be made by reaction of a suitable aralkyl reagent, such as a haloalkyl benzene or a phenylalkene with phenol or a halophenol as appropriate using suitable catalysts or coreagents such as hydrogen halides (for example as described in U.S. Pat. No. 2,247,402). The crude aralkyl substituted products will often be mixtures of compounds having varying numbers of, and ring location of, substituents. Steric hindrance may make it difficult to manufacture pure tri-aralkyl phenols and the products may need to be purified e.g. by distillation, after manufacture. In practice, mixed products may be used to make compounds of and used in the invention allowing for the intermediate properties (as compared with pure) materials.

The compounds of and used in the present invention can be made by methods generally known for making compounds with similar structures.

For compounds based on polymerised fatty acid hydrophobes, particularly those of the formula (Ia) above, a particularly convenient reaction is the reaction of the polymerised acid with a (hydroxyl ended) polyalkoxylated amine, if desired in the presence of an esterification catalyst, such as a base. The intermediate polyalkoxylated amine can be made by reaction between an amine, generally a secondary amine (because primary amines have two alkoxylation reaction sites generally giving two polyalkoxylate chains) or a hydroxy substituted tertiary amine (generally itself made by alkoxylation of a secondary amine), and the corresponding alkylene oxide, as appropriate in the presence of an alkoxylation catalyst, usually a basic catalyst e.g. alkoxide e.g. methoxide, or NaOH or KOH, forming alkoxide in situ on removal of water. The polyalkoxylation may be carried out in more than one stage to allow for the build up of product mass with increasing molecular weight.

Remaining acid e.g. COOH, groups (not reacted to form esters) may be neutralised with base or alkali, particularly alkali metal, ammonium, amine or quaternary amine alkali, either wholly or in part to form a suitable salt.

For compounds based on aralkylphenyl hydrophobes, particularly those of the formula (Ib) above, the compounds can be made by a variety of routes. Generally these will involve either reacting a preformed aralkylphenyl polyalkoxylate, which may be based on the phenol, itself, a hydroxy carboxylic acid ester of the phenol (which can be made by reacting the phenol with a hydroxycarboxylic acid or a reactive derivative such as a lactone—where available), or a carbonate ester of the phenol (which can be made by reacting the phenol with a carbonate ester reagent such as a dialkyl carbonate or a cyclic glycol carbonate) particularly a polyethoxylate, to add the terminal amine functionality desired or by reacting an amine ended polyalkoxylate, usually a polyethoxylate with a reactive derivative of the precursor aralkylphenol. Reaction routes starting with aralkylphenol polyalkoxylates, particularly polyethoxylates, include:

i if necessary cap the polyalkoxylate with propylene oxide and then directly aminate the terminal secondary hydroxyl group. The amination can be carried out using ammonia or a primary or secondary amine under reducing conditions typically over a nickel e.g. Raney Nickel, catalyst usually at relatively high pressure e.g. ca 200 Bar, and temperature, e.g. ca 250° C. When the immediate product is a primary or secondary amine it may be further alkylated conventionally.

ii react the polyalkoxylate with a halocarboxylic acid, particularly an -halocarboxylic acid such as chloroacetic acid (or a salt such as an alkali metal, e.g. Na or K, salt), and react the carboxyl ended intermediate with a hydroxyl or amine ended (tertiary) amine;

iii oxidise the terminal (ethoxylate) group of the polyalkoxylate chain to convert it to a carboxylate group then react the carboxyl ended intermediate with a hydroxyl or amine ended (tertiary) amine;

iv react the polyalkoxylate with a dicarboxylic acid reagent e.g. an anhydride, such as succinic anhydride, and then react the carboxyl ended intermediate with a hydroxyl or amine ended (tertiary) amine;

v react the polyalkoxylate with epi-halohydrin (especially epi-chlorohydrin under alkoxylation conditions followed by nucleophilic displacement of the terminal halogen (chlorine) atom with an amine, particularly a secondary amine.

Aralkylphenol alkoxylates may be made by conventional alkoxylation of the corresponding precursor aralkylphenol. Where carbonate esters are used these may be made by reacting the precursor phenol with a carbonate ester such as a dialkyl carbonate (giving a mixed phenol alcohol carbonate ester that may be reacted with a pre-formed alkoxylated amine intermediate), or a cyclic glycol carbonate (giving a mixed phenol glycol carbonate which may be alkoxylated and reacted further as described above). As with alkoxylations in making polymerised fatty acid hydrophobe products, polyalkoxylation may be carried out in more than one stage to allow for the build up of product mass with increasing molecular weight.

Quaternary amino, betaine and N-oxide groups may be made by conventional reactions from the tertiary amine ended products. Thus quaternary amines can be made by reacting the tertiary amine ended product with conventional alkylating agents such as dialkyl, particularly dimethyl, sulphate of alkyl, particularly methyl, halide, particularly chloride. Betaines can be made by reacting the tertiary amine ended product with a halocarboxylic acid, particularly an -haloacid such as chloroacetic acid (or a salt such as an alkali metal, e.g. Na or K, salt), or by oxidation of a terminal ethylene oxide residue. N-oxides can be made by reacting the tertiary amine ended product with a molar equivalent of aqueous hydrogen peroxide.

As used it is generally convenient that the surfactant compound is neutral or near neutral e.g. having an aqueous pH of from 4 to 9. Generally extremes of pH either highly acid or highly alkali will be avoided to reduce the likelihood of destroying the surfactant compound, particularly ester forms of dispersant, by hydrolysis.

The compounds can be used to make dispersions which find particular use in dispersing agrochemicals, generally of particulate solids, usually finely divided particulate solids, particularly an agrochemical active, in an aqueous medium, usually water, which may contain other components of a formulation. Accordingly, the present invention provides a dispersion of a solid, particularly an agrochemical active, in a liquid phase, particularly an aqueous liquid phase which includes as a dispersing agent one or more compounds including an amine ended polyalkylene glycol hydrophile(s) linked to a $C_{22}$ to $C_{60}$ mainly hydrocarbyl hydrophobe, particularly one which is composite a hydrocarbyl hydrophobe, more particularly a hydrophobe including branched and/or cyclic groups or constituents, in particular where the hydrophobe of the dispersing agent is derived from a polymerised fatty acid, particularly a fatty acid dimer and/or trimer and/or an aralkyl substituted phenol. Where the hydrophobe is derived from a polymerised fatty acid, it is particularly of the formula (I) above.

The dispersants can be used in various forms of dispersion in agrochemical applications and the invention accordingly includes an agrochemical dispersion, in which at least one dispersant of the invention, particularly at least one compound of the formula (I), and desirably of one of the formulae (Ia) or (Ib), is included as a dispersant. Within this, more particularly the invention includes:

i an agrochemical dispersion in which a solid component particularly an active agrochemical, is dispersed in a liquid, particularly an aqueous, phase; or ii an agrochemical suspoemulsion including an agrochemically active material which is dispersed in a first liquid, particularly an aqueous, component, a second liquid component being emulsified in the first liquid component.

The agrochemically active material(s) included in the emulsions and/or dispersions in this aspect of the invention can include one or more plant growth regulators, herbicides, and/or pesticides, for example insecticides, fungicides, acaricides, nematocides, miticides, rodenticides, bactericides, molluscicides and bird repellents. Examples of classes of actives include:

Herbicides: including water soluble, particularly non-selective, herbicides (used with water dispersible components in this invention), particularly N-phosphonomethyl glycine herbicides e.g. Glyphosate and Sulfosate, the glufosinate, bipyridyl e.g. Paraquat, phenoxy and imidazolidinonyl types of non-selective herbicides, triazines, substituted ureas, sulphonyl ureas, pyridine carboxylic acids, aryloxy alkanoic acids, 2-(4-aryloxy-phenoxy)propionic acids, bis-carbamates;

Fungicides: including thiocarbamates, particularly alkylenebis(dithiocarbamate)s, strobilurins, dicarboximides, benzimidazoles, azoles, inorganic fungicides e.g. potassium phosphite;

Insecticides including benzoyl ureas and

Acaricides including tetrazines.

Particular applications of the dispersant of and used in the invention in agrochemicals include:

Aqueous dispersions of solid components which can be insoluble actives, particularly fungicides or herbicides, but may be non-agrochemically active insoluble solid components. The proportion of the dispersing agent will typically be from 2 to 8%, more usually from 2 to 5%, by weight of the dispersion. Such dispersions may be incorporated into suspoemulsions (see below). Suspoemulsions including at least one liquid and at least one solid disperse phase in an aqueous continuous phase are particularly suitable for agrochemical formulations which include an oil soluble active and a solid water insoluble (usually also oil insoluble) active, with the oil soluble active present as an emulsion and the solid water insoluble active present as dispersed particles. The proportion of polymerised fatty acid dispersant is typically from 0.1 to 10%, more usually form 0.5 to 1.5% by weight of the emulsion. Suspoemulsions will commonly also include relatively hydrophilic surfactant e.g. one having an HLB value of 10 or more such as hydrophilic alcohol alkoxylate and/or anionic surfactants, particularly phosphate and/or sulphate ether anionic surfactants, and/or taurate and/or sarcosinate anionic surfactants, and/or fatty amine 2 to 10 ethoxylates and/or amphoteric surfactants. Such surfactants are typically used at from 1 to 10%, more usually from 3 to 5%, by weight of the suspoemulsion, to aid emulsification of the oil disperse phase in the (usually) aqueous continuous phase.

Oil dispersible (OD) concentrate formulations are formulations which include an active dispersed in an oil. In order to inhibit or prevent the solid active from precipitating as a separate layer in the OD concentrate before dilution for spraying, they typically contain an oil phase dispersant surfactant and commonly also an oil phase structurant or thickener.

On dilution with water to form a spray mix, e.g. as when making up a tank mix for spraying, the oil forms an oil in water emulsion and the dispersed active, typically having a particle size similar to that of the oil emulsion droplets, forms a dispersion in the dilution water aqueous phase. To provide a suitable level of stability after dilution, the OD formulation will typically further include an oil in water emulsifier and an aqueous phase dispersant for the solid active (it is possible that both these functions may be provided by a single material). In addition adjuvants, which are commonly surfactants, may be included in OD formulations.

We have found that the surfactants of the present invention can be used as aqueous (hydrophilic) dispersants in OD concentrate formulations. They appear not to significantly interfere with the stability of the OD concentrate and become available and effective as dispersants for the water insoluble active on dilution to form a spray mix. Oil dispersion concentrates do not usually include dissolved electrolytes as they are usually insoluble in oils, though electrolyte material may be included as dispersed solid particles. Of course the diluted spray formulations may include (generally separately added) electrolyte and the stability advantage of the dispersants of the present invention can benefit such diluted formulations. The oil in such OD concentrate formulations can be a conventional carrier oil, a crop oil or a suitable liquid active e.g. 2,4-D.

In these agrochemical applications, the dispersions can include other components particularly surfactants, as adjuvants or wetting agents. Examples include:

anionic surfactants e.g. alkali metal or alkali earth metal salts of sulphonated hydrocarbons such as alkyl benzene sulphonates particularly Ca dodecylbenzene sulphonate, typically included at from 0.1 to 10%, more usually from 2 to 3%, by weight of the emulsion; and/or alcohol alkoxylates such as those based on $C_8$ to $C_{22}$, particularly $C_{12}$ to $C_{18}$, alcohols, which may have straight or branched, usually alkyl, chains, and which are alkoxylated with ethylene oxide, propylene oxide or copolymeric chains including residues of both ethylene oxide and propylene oxide, which may be block or random (statistical) copolymeric chains, commercially available examples include Synperonic A11/A20 (Croda), typically included at from 0.1 to 10%, more usually from 2 to 3%, by weight of the emulsion; and/or fatty amine polyethoxylates such as Atlas G3780A (Croda) and/or alkyl, particularly $C_8$ to $C_{12}$ alkyl, polyglucosides.

In agrochemical compositions, the dispersants of the invention can be used alone or in combination with other dispersants, but desirably, the proportion of dispersant of the invention is at least 50%, more usually at least 75%, by weight of the total dispersant used in the composition.

When electrolyte is included in the dispersions of the invention it is typically a fertilizer, particularly a water soluble inorganic fertilizer, and/or a water soluble ionic pesticide (electrolyte pesticide), usually a herbicide, and most commonly a foliar applied (post-emergence) herbicide. Typically the concentration of electrolyte in the concentrate composition is from 1 to 50%, more usually 5 to 40%, particularly 10 to 30% by weight of the total composition.

Among water soluble fertilisers that form electrolyte solutions in water are the common water soluble inorganic fertilizers that provide nutrients such as nitrogen, phosphorus, potassium or sulphur. Examples of such fertilizers include:

for nitrogen as the nutrient:
nitrates and or ammonium salts such as ammonium nitrate, including in combination with urea e.g. as Uram type materials, calcium ammonium nitrate, ammonium suphate nitrate, ammonium phosphates, particularly mono-ammonium phosphate, di-ammonium phosphate and ammonium polyphosphate, ammonium sulphate, and the less commonly used calcum nitrate, sodium nitrate, potassium nitrate and ammonium chloride;

for potassium as the nutrient:
potassium chloride, sulphate e.g. as mixed sulphate with magnesium, phosphates, particularly potassium dihydrogen phosphate and potassium polyphosphate and less commonly potassium nitrate;

for phosphorus as the nutrient:
acidic forms of phosphous such as phosphoric, pyrophosphoric or polyphosphoric acids, but more usually salt forms such as ammonium phosphates, particularly mono-ammonium phosphate, di-ammonium phosphate, and ammonium polyphosphate, potassium phosphates, particulalry potassium dihydrogen phosphate and potassium polyphosphate;

for sulphur as the nutrient:
ammonium sulphate and potassium sulphate, e.g. the mixed sulphate with magnesium.

Fertilisers may be included in diluted formulations at relatively low concentrations or as more concentrated solutions, which at very high levels may include solid fertiliser as well as solution.

Where high concentrations of electrolyte are desired, particularly of fertiliser, a dispersion concentrate of the invention, which may be either water based or oil based, may be diluted into the aqueous electrolyte solution, optionally including further electrolyte, particularly fertiliser, as solid. This approach is useful where the aqueous medium is a solution of electrolyte such as of water soluble electrolyte agrochemical active such as glyphosate and/or, and especially, of inorganic electrolyte fertiliser, particularly nitrogen based fertiliser, such as ammonium sulphate, ammonium nitrate e.g. as in Uram (urea and ammonium nitrate), and similar materials. The fertiliser may be sufficiently concentrated that it is partly present as a solid dispersion in the water component. Such systems are used particularly in pre-emergence weed burn off in cultivating crops such as maize, especially in low/no-till growing regimes, where combining concentrated fertiliser application and weed burn down can be of high value.

Other water soluble nutrient containing compounds (commonly identified as "micronutrients") may also be included e.g. to provide minor or trace nutrients to the formulation. Similarly, water soluble buffering and chelating agents such as ammonium and alkali metal citrates, gluconates, lactates, and polyacryates may be included as part or all of the electrolyte component of the fomurlation.

When present, the proportion of anhydrous fertiliser in the total concentrate formulation is typically from 5 to 40, more usually, 10 to 35, particularly 15 to 30, % by weight based on the concentrate.

Water soluble ionic pesticides include particularly water soluble non-selective herbicides such as the glyphosate, glufosinate and paraquat and diquat types. Glyphosate herbicides are usually water soluble agrochemically acceptable salt, commonly alkali metal e.g. sodium or potassium, amine e.g. isopropylamine, or trimesium, salts of N-phosphonomethyl glycine. The glufosinate type of herbicides are phosphinyl amino acids such as Glufosinate [2-amino-4-(hydroxymethyl-phosphinyl) butanoic acid] particularly as the ammonium salt. The paraquat and diquat types of herbicides are bipyridinium compounds particularly Paraquat [1,1'-dimethyl-4,4'-bipyridinium] and Diquat [1,1'-dimethyl-2,2'-bipyridinium].

Typically, agrochemical dispersion concentrate or suspoemulsion formulations of the invention will include from 0.25 to 8%, more usually from 0.5 to 4% dispersant and from 0.5 to 50%, more usually from 1 to 20% of one or more dispersed agrochemically active component(s). When present water soluble electrolyte, which, as noted above, may also be agrochemically active, will typically be present at from 1 to 30% more usually from 2.5 to 25%. Other, optional, components include adjuvants typically present at 1 to 30%, more usually from 2 to 20%; wetting agent(s) at up to 3%; antifreeze agent(s) at up to 10%; antisettling agent(s) at up to 10%; antifoaming agent(s) at up to 1%. Generally the balance of the formulation will be water. All these percentages are by weight on the total weight of the concentrate formulation.

The compounds of the invention, particularly the fatty acid di-/tri-mer derivatives especially of the formula (Ia), may also be used as adjuvants, particularly for plant growth regulator, pesticide or herbicide agrochemicals, notably water soluble pesticides and herbicides, such as the glyphosate, glufosinate and paraquat/diquat type herbicides. Other actives that may be used include those set out above (in connection with agrochemical dispersions) or as described in WO96/16930 A, or WO 01/05224 A.

When used as adjuvants the compounds of the invention will typically be include in an agrochemical formulation in an amount of 0.2 to 10%, more typically 0.3 to 7% and particularly 0.75 to 5%, by weight of the (concentrate) formulation. On dilution to produce a spray the amount of the compounds in this use will typically be from 0.002 to 0.25%, particularly 0.005 to 0.2%, especially 0.01 to 0.15%, by weight of the diluted spray formulation.

When used as adjuvants, the compounds of the invention, may, in particular, be used with active agrochemicals that are formulated in aqueous solution, as with the water soluble herbicides mentioned above. However, other convenient formulation types may be used such as oil solution, aqueous dispersion, oil dispersion or combination formulation types such as suspoemulsions and combined solution dispersion formulations i.e. including both dissolved and dispersed actives. Formulated as concentrates, such formulations thus include aqueous and oil based solution concentrates, aqueous and oil based dispersion concentrates, aqueous solution dispersion concentrates and suspoemulsion concentrates. As described above in conjunction with dispersion concentrates, all these types of concentrate are typically diluted with 10 to 10,000 times the weight of the concentrate of water before spraying. Of course, when used as dispersants for solid (substantially water insoluble) agrochemicals in formulations, particularly where the formulations include other e.g. water soluble agrochemicals, the compounds of the invention may act as both dispersants and adjuvants.

Other, optional, components include further adjuvants typically present at 1 to 30%, more usually from 2 to 20%; wetting agent(s) at up to 3%; antifreeze agent(s) at up to 10%; antisettling agent(s) at up to 10%; antifoaming agent(s) at up to 1%. Generally the balance of the formulation will be water. All these percentages are by weight on the total weight of the concentrate formulation.

As mentioned above the concentrate formulations will usually be diluted (typically with from 10 to 10000 times the weight of the concentrate of water) to make a spray formulation for spray application to the desired crop or location. Further components may be added at or after dilution as components of the spray formulation, commonly referred to as "tank mix" additives or components. One common type of tank mix additive are adjuvants especially adjuvant oils, surfactants, water conditioning agents and drift reduction agents.

The diluted formulation may include further components, e.g. added to the spray tank mix, including crop oil concentrates, antifoam agents or other typical tank mix additives.

The following Examples illustrate the invention. Unless otherwise indicated all parts and percentages are by weight.
Materials
  polymerised fatty acids
  TA1 trimer acid—containing 75% (min) trimer acid and (up to) 25% dimer acid—(AV 186.1 mg(KOH) g$^{-1}$) Pripol 1040 ex Croda
  tristyryl phenol ethoxylates
  TSPE tristyryl phenol 16-ethoxylate, Soprophor BSU (ex Rhodia)
  amine alkoxylates
  AA1 diethylethanolamine 12.4-ethoxylate
  AA2 diethylethanolamine 17.8-ethoxylate
  AA3 diethylethanolamine 22.7-ethoxylate
  AA4 diethylethanolamine 10-ethoxylate These amine alkoxylates were made by alkoxylating the precursor dialkylethanolamine—itself made by reaction of ethylene oxide with the corresponding dialkylamine—as appropriate in one or more stages using alkali catalysis.

Test Methods

Acid Value—was determined according to American Oil Chemists Society, (AOCS) 1989 methods Ca 5a-40 and Cd 3b-76 and Standard Methods for the Analysis of Oils, Fats and Derivatives, (IUPAC) 1979 method 2.201 and the results given as AV in (mg(KOH)·g$^{-1}$).

Hydroxyl Value—was determined by acetylating free hydroxyl groups in a sample of known weight with a known excess of acetic anhydride (determined by blank titration), adding water to hydrolyse unreacted anhydride, and back titrating the acetic acid liberated with standard NaOH solution using phenolphthalein indicator. The results given as OHV in mg(KOH)·g$^{-1}$.

SYNTHESIS EXAMPLES

Synthesis Example SE1

TA1 (427.5 g; 0.5 mol) and AA1 (332.4 g; 0.5 mol) were added to a stirred 700 ml flanged flask equipped with a nitrogen blanket, thermometer and condenser (to remove water of reaction) and heated to 190° C. under nitrogen. The heating was continued until a constant acid value was achieved (after about 6 hours). The reaction mixture was allowed to cool and was discharged to obtain 750 g of the desired product. The final acid value (64.1 mg(KOH)·g$^{-1}$) confirms the product as the monoester (theoretical value 65.6 mg(KOH)·g$^{-1}$).

Synthesis Examples SE2 to SE4

These products were made by the general method described in Synthesis Example SE1 but using amine alkoxylates AA2, AA3 and AA4 as starting materials to give compounds SE2, SE3 and SE4.

Synthesis Example SE5

Betaine Derivatives

SE1 (346.4 g; 0.231 mol) and sodium chloroacetate (26.9 g; 0.231 mol) were added to a stirred 500 ml flask equipped with a nitrogen blanket, thermometer and condenser and heated to 150° C. under nitrogen for at least 6 hours (or until the mixture became homogeneous) and the reaction mixture allowed to cool to give 373 g of the title compound with an AV of 63.1 mg(KOH)·g$^{-1}$.

Synthesis Example SE6 and SE7

These products were made by the general method described in Synthesis Example SE5, but using mono-ester compounds SE2 and SE3 as starting materials to give compounds SE6 and SE7.

Synthesis Example SE8

N-oxide Derivatives

SE1 (40.58 g; 0.027 mol) was added to a stirred 100 ml flask equipped with a nitrogen blanket, thermometer and condenser and heated to 60° C. Hydrogen peroxide (1.82 g; 0.027 mol) was added dropwise over a period of about 10 minutes and the mixture stirred under nitrogen at 60° C. for a further 2 hours and then allowed to cool to give 40 g of the desired product with an AV of 62.6 mg(KOH)·g$^{-1}$.

Synthesis Example SE9 and SE10

These products were made by the general method described in Synthesis Example SE8, but using mono-ester compounds SE2 and SE3 as starting materials to give compounds SE9 and SE10.

Synthesis Example SE11

TSPE (211.2 g; 0.19 mol) was charged to a 500 ml round bottom flask equipped with agitator, nitrogen blanketing, condenser and isomantle. The contents were heated to 40° C. and succinic anhydride (19.4 g; 0.19 mol) added through a dropping funnel over 10 minutes and then the mixture was heated to 120° C. and held at this temperature for 1 hour before cooling to room temperature. The product had OHV 0.8 mg(KOH)·g$^{-1}$ and AV of 46.7 mg(KOH)·g$^{-1}$ (theoretical AV=47.2 mg(KOH)·g$^{-1}$).

Diethylethanolamine (40 g; 0.34 mol) was added to the flask and the condenser reconfigured for take-off. The contents were heated to 180° C. and held at this temperature until no more distillate was observed. The reaction was monitored by hydroxyl and acid value measurements. [An excess of diethylethanolamine was used because the boiling point of diethylethanolamine is close to the esterification temperature.] The product was obtained as a pale yellow slightly hazy liquid and was used without further purification. Based on the measured AV the product represented ca. 91% conversion of ester intermediate.

Details of all the synthesised compounds are given in Tables SE1a to SE1d below.

TABLE SE1a

| SE No | Acid | Am alkox. | mol ratio[1] | Time (hr) | AV |
|---|---|---|---|---|---|
| SE1 | TA1 | AA1 | 1 | 9 | 61 |
| SE2 | TA1 | AA2 | 1 | 6 | 54.8 |
| SE3 | TA1 | AA3 | 1 | 11 | 47 |
| SE4 | TA1 | AA4 | 1 | 6 | 69.1 |

[1]molar ratio of ethoxylated amine:acid

TABLE SE1b (betaines)

| SE No | start matl | Time (hr) | AV |
|---|---|---|---|
| SE5 | SE1 | 6 | 63.1 |
| SE6 | SE3 | 3 | 48.4 |
| SE7 | SE4 | 4 | |

TABLE SE1c (N-oxides)

| SE No | start matl | Time (hr) | AV |
|---|---|---|---|
| SE8 | SE1 | 2 | 62.6 |
| SE9 | SE2 | 2 | 54.2 |

TABLE SE1c (Tristyrylphenol derivative)

| SE No | AV | OHV |
|---|---|---|
| SE11 | 3.9 | 0 |

APPLICATION EXAMPLES

Dispersions

Materials
Dispersants
SExx numbers identifies dispersant surfactants made in the corresponding Synthesis Example
Comp1 acrylic copolymer with PEG side chains, Atlox 4913 ex Croda
Comp2 tristyrylphenol ethoxylate phosphate ester, Sorophor FLK ex Rhodia
Dispersed Solids (DS)
Act1 neonicotinoid insecticide, Imidacloprid (SG 1.54)
Act2 triazole fungicide, Tebuconazole (SG 1.25)
Act3 carbamate insecticide, Carbaryl (SG 1.2)
Act4 triazine herbicide, Atrazine (SG 1.19)
Act5 imidazole fungicide, Iprodione (SG 1.43)
TiO2 titanium dioxide pigment (TR28 ex-Tioxide)—not an agrochemical active but used in testing as more dense (SG ca 2.5) than typical water insoluble solid agrochemicals.
Wetting Agents
Wetter alkoxylated alcohol nonionic surfactant, Synperonic 10/6 ex Croda
Electrolyte
Gly 50% wt aqueous solution of glyphosate potassium salt
AMS ammonium sulphate
Other Materials
NSC naphthalene sulphonate condensate as sodium salt, Morwet D-425 ex Akzo
TAE tallow amine ethoxylate adjuvant, Atlox G-3780A ex Croda
Test Methods
Dispersions were made up by adding the desired amount of dispersant to an aqueous dispersion of the solid to be dispersed if desired including an appropriate amount of a wetting agent. The combination was mixed in a high shear mixer (typically an UltraTurrax mixer) e.g. at 10000 rpm (ca 167 Hz) for one minute, and then milled (typically in an Eiger mini-mill colloid mill) e.g. for 15 minutes, rolled for several hours and left overnight to equilibrate.

Samples of the dispersions were tested by adding various materials to assess the ability of the dispersants to be formulated and used in practical situations.

Electrolyte Tolerance—was assessed by adding Gly as electrolyte to samples of dispersions (prepared as described above) to give a predetermined level of electrolyte in the overall formulation. For example to provide a level of 5% glyphosate, 2 g Gly was added to 18 g dispersion in a small bottle which was then capped and rolled for 2 to 3 hours then visually assessed. The rheology (particularly zero shear viscosity) of those that appeared homogenous was assessed using a Bohlin CVO instrument.

Suspensibility—was assessed by adding 5% of dispersion to a measuring cylinder containing either 1000 ppm $CaCO_3$ water (W1), 1000 ppm $CaCO_3$ water with 5% ammonium sulphate (W2) or 5% ammonium sulphate (W3). The measuring cylinder was then inverted (10 or 20 times) and sedimentation assessed after 30 minutes (30 min), 2 hours (2 hr) or 24 hours (24 hr) as the depth in mm of the sediment layer at the bottom of the cylinder.

Particle size—was measured on samples of dispersion using a Malvern (2000) particle sizer. Aged samples are indicated by the aging time in months e.g. 1 m, and the aging temperature as ambient (Amb) or in ° C. (xx° C.).

Application Example AED1

Dispersions of a variety of solids were made up using dispersants of the invention and comparative dispersants using the following proportions of materials:

| material | amount (wt %) |
|---|---|
| Dispersant | 0.5 or 1.25 (depending on solid) |
| Act4 | 50 |
| Wetter | 0.375 |
| Glyphosate K salt | from 0 to 20% |
| Water | to 100 |

The dispersions were mixed in an UltraTurrax, and milled in an Eiger mini-mill, rolled for several hours and left overnight to equilibrate. For the dispersions of $TiO_2$, 0.5% active dispersant (1% of dispersant solution) and for agrochemical active ingredients, 1.25% active dispersant (2.5% of dispersant solution), were used. The results of testing these dispersions are set out in Table(s) AED1a to AED1c below.

TABLE AED1a (Zero Shear Viscosity)

| | | | Viscosity (mPa) | | | | |
| | | | Glyphosate added (wt %) | | | | |
| AE No | Dispersant | Active | 0 | 5 | 10 | 15 | 20 |
|---|---|---|---|---|---|---|---|
| AE1C1a | Comp1 | Act1 | 0.12 | 4.2 | 147 | (1) | (1) |
| AE1C2a | Comp2 | | (1) | (1) | (1) | (1) | (1) |
| AE1.1 | SE1 | | 0.2 | 0.045 | 0.018 | 0.016 | 0.11 |
| AE1.2 | SE5 | | 0.03 | 0.03 | 0.02 | 0.02 | 7.63 |
| AE1C1b | Comp1 | Act2 | 0.046 | 3.99 | 2400 | (1) | (1) |
| AE1C2b | Comp2 | | 0.37 | 11.7 | 416 | 2954 | (1) |
| AE1.3 | SE1 | | 0.23 | 0.14 | 0.053 | 1.41 | 21.99 |

TABLE AED1a-continued (Zero Shear Viscosity)

| AE No | Dispersant | Active | Viscosity (mPa) Glyphosate added (wt %) | | | | |
|---|---|---|---|---|---|---|---|
| | | | 0 | 5 | 10 | 15 | 20 |
| AE1.4 | SE11 | | 0.04 | 11.6 | 80.1 | 740 | 2123 |
| AE1C1c | Comp1 | Act4 | 0.059 | 184 | ca 6000 | (1) | (1) |
| AE1C2c | Comp2 | | 0.40 | 210.4 | (1) | (1) | (1) |
| AE1.5 | SE1 | | 6.61 | 0.19 | 0.05 | 0.05 | 0.33 |
| AE1.6 | SE5 | | 2.04 | 0.42 | 0.05 | 0.65 | 155 |
| AE1.7 | SE11 | | 80 | (1) | (1) | (1) | (1) |
| AE1C1d | Comp1 | Act5 | 0.01 | 2.55 | 933 | (1) | (1) |
| AE1.8 | SE1 | | 0.91 | 0.10 | 0.04 | 0.93 | 0.95 |
| AE1.9 | SE5 | | 0.05 | 0.21 | 0.05 | 0.8 | 93.8 |

(1) dispersion very thick - rheology not assessed

TABLE AED1b (Particle size)

| Ex No | Dispersant | Active | Particle size D[4, 3] (m) Glyphosate (wt %) | | | | |
|---|---|---|---|---|---|---|---|
| | | | 0 | 5 | 10 | 15 | 20 |
| AE2C1 | Comp 1 | Act4 | 4.8 | 8.5 | 35.3 | 162.4 | 69.4 |
| AE2a | SE1 | | 5.1 | 5.1 | 5.1 | 5.4 | 5.5 |
| AE2C2 | Comp 2 | TiO2 | 0.13 | — | — | — | 3.5 |
| AE2b | SE1 | | 0.24 | — | — | — | 0.24 |

TABLE AED1c (Suspensibility - 10 inversions)

| | | Sedimentation (mm) | | | |
|---|---|---|---|---|---|
| | | W1 | | W2 | |
| SD | Dispersant | 30 min | 2 hr | 30 min | 2 hr |
| Act1 | Comp1 | 1 | 2 | 2 | 7 |
| | Comp2 | 11 | 13 | 13 | 18 |
| | SE1 | 2 | 2 | 2 | 5 |
| Act2 | Comp1 | 1 | 3 | 2 | (2) |
| | Comp2 | 1 | 3 | 18 | 10 |
| | SE1 | 1 | 3 | 1 | 7 |

(2) Could not be measured - the top of the sediment could not be seen because the dispersion was too opaque.

Application Example AED2

A model herbicide formulation—using Atrazine (Act4) and Glyphosate (isopropylamine salt) actives was made up using the following proportions of materials:

| Component | w/w % |
|---|---|
| Act4 | 30 |
| Dispersant | 2.25 |
| NSC | 0.75 |
| Glyphosate-IPA Salt (40% active) | 57 |
| TAE | 9.12 |
| Water | 0.88 |

The glyphosate is present as its isopropylamine salt at the maximum level formulation space allows as 23 wt % active ingredient (57 wt % of 40 wt % active solution).

The ingredients were high shear mixed, milled for 15 minutes at 5000 rpm and assessed for particle size, storage stability and suspensibility. The results of these tests are set out in Tables AED2a and AED2b below.

TABLE AED2a

| | | Particle size | | | | | |
|---|---|---|---|---|---|---|---|
| | | Initial | | 2 m (Amb) | | 1 m (54° C.) | |
| Ex No | Disp. | D[3, 2] (m) | D[4, 3] (m) | D[3, 2] (m) | D[4, 3] (m) | D[3, 2] (m) | D[4, 3] (m) |
| AED2.1 | SE1 | 3.5 | 5.5 | 3.76 | 5.21 | 5.23 | 13.96 |
| AED2.C.1 | Comp1 | 4.6 | 24.1 | 4.5 | 13.48 | 7.1 | 20.93 |

These data show that neither dispersion showed a significant particle size change after 2 months storage at ambient temperature, the dispersant of the invention gave a finer dispersion with a narrower particle size range and that the dispersion stabilised with the dispersant of the invention remained stable after storage for one month at 54° C. with only a small increase in particle size, but the particle size of the dispersion stabilised with the comparative dispersant increased significantly under these conditions. Further a similar storage performance advantage for dispersants of the invention was seen under freeze/thaw and low temperature storage conditions.

TABLE AED1b (Suspensibility - 20 inversions)

| Active | Dispersant | Sedimentation (mm) @24 hr | | |
|---|---|---|---|---|
| | | W1 | W2 | W3 |
| Act4 + Glyphosate | SE1 | 1 | 2 | 2 |
| | Comp1 | 1 | 2 | 2 |

APPLICATION EXAMPLES

Adjuvancy

Materials
SExx numbers identify adjuvant surfactants made in the corresponding Synthesis Example
FAE fatty ($C_{18}$) amine polyethoxylate, Atlas G3780A ex Croda
Gly glyphosate herbicide as isopropylamine salt ex Aldrich Method A greenhouse trial was run to evaluate the effectiveness of the surfactants of the invention as adjuvants for Glyphosate in controlling the growth of (non-roundup ready) oil seed rape plants (*Brassica napus*). The trial used surfactant of the invention (SE1) and control adjuvant (FAE) at 3 rates, with 3 rates of glyphosate application, and controls including 3 glyphosate rates without surfactant, all grown in randomised blocks. 10 replications were used for each application, with 1 pot (7×7×8 cm) per plot and at least 4 plants per pot, in Levington M2 medium. The greenhouse conditions of temperature and humidity were recorded and watering was carried out by capillary matting. Additional lighting was provided over natural daylight. The glyphosate treatments were carried out using a pre-calibrated Mardrive greenhouse cabinet sprayer at a volume rate of about 200 l.ha$^{-1}$. The plants were visually assessed for foliar damage (rated as % damage) and other symptoms at 7, 15 and 21 days after application and the above ground fresh weight was measured at 21 days after application and the % control of growth (compared with untreated controls—average weight 23.3 g) was calculated.

The type and application rate (Rate in g.ha$^{-1}$) of nominally 100% adjuvant, the application rate (Rate in g.ha$^{-1}$ active) of glyphosate, the glyphosate to adjuvant weight ratio (G:A) applied to the test plants and the visual assessment (%), and the % control are set out in Table AEA1 below.

TABLE AEA1

| Ex No | Adjuvant Type | Adjuvant Rate | Glyphosate Rate | G:A | % damage 15 d | % damage 21 d | % damage 28 d | % control 28 d |
|---|---|---|---|---|---|---|---|---|
| AEA.1a | SE1 | 62.5 | 125 | 2:1 | 0.5 | 0 | 0 | −9.3 |
| AEA.1b | | 125 | 250 | | 9 | 36 | 24 | 33.1 |
| AEA.1c | | 250 | 500 | | 18 | 61 | 86 | 81.9 |
| AEA.1d | | 31.25 | 125 | 4:1 | 0.5 | 4 | 7 | 19.9 |
| AEA.1e | | 62.5 | 250 | | 9 | 24 | 17 | 2.1 |
| AEA.1f | | 125 | 500 | | 19 | 61 | 82 | 80.5 |
| AEA.1g | | 15.625 | 125 | 8:1 | 0 | 2 | 9 | 20.8 |
| AEA.1h | | 31.25 | 250 | | 2.5 | 17 | 17 | 30.4 |
| AEA.1i | | 62.5 | 500 | | 14 | 54 | 74 | 67.5 |
| AEA.C1a | FAE | 62.5 | 125 | 2:1 | 0 | 2 | 0 | −14.5 |
| AEA.C1b | | 125 | 250 | | 5.5 | 21 | 0 | 5.2 |
| AEA.C1c | | 250 | 500 | | 20 | 69 | 85 | 83.0 |
| AEA.C1d | | 31.25 | 125 | 4:1 | 0 | 3 | 0 | −6.4 |
| AEA.C1e | | 62.5 | 250 | | 4.5 | 4 | 0 | −1.9 |
| AEA.C1f | | 125 | 500 | | 13 | 49 | 62 | 60.3 |
| AEA.C1g | | 15.625 | 125 | 8:1 | 1 | 2 | 0 | −10.2 |
| AEA.C1h | | 31.25 | 250 | | 2.5 | 5 | 7 | −2.4 |
| AEA.C1i | | 62.5 | 500 | | 14 | 46 | 58 | 59.4 |
| AEA.C2a | None | 0 | 125 | — | 0 | 5 | 0 | 0.2 |
| AEA.C2b | | 0 | 250 | — | 1.5 | 5 | 0 | −6.4 |
| AEA.C2c | | 0 | 500 | — | 11 | 33 | 52 | 49.5 |

APPLICATION EXAMPLES

Oil Dispersible Concentrates

Materials

SExx numbers identify adjuvant surfactants made in the corresponding Synthesis Example Oils Oil1 partially aromatic hydrocarbon solvent, Solvesso 200ND ex Exxon Mobil Oil2 methyl oleate Structurants Clay1 'self-activated' bentonite clay, Bentone 1000 ex Elementis Clay2 unactivated*bentonite clay, Bentone 38V ex Elementis
* for use Clay2 was activated by including 33% by weight on the clay propylene carbonate in the formulation.

Surfactants

Surf1 oil in water emulsifier, sorbitol hexaoleate 40-EO, Atlas G1086 ex Croda

Surf2 oil phase dispersant, polyhydroxystearic acid, Hypermer LP1 ex Croda

Test Methods

Rheology—was assessed using a Bohlin Rheometer and the yield stress (YS in) and zero shear viscosity (Visc in mPa·s) were reported Stability—of oil dispersions was tested by storing dispersion samples at ambient (Amb) or elevated temperature (54° C.), with assessment of the % oil separation after 1 day (1 d), 1 week (1 w) and 1 month (1 m). A "pass" on this test is less than 10% oil separation.

Dispersibility—of OD formulations was assessed by diluting the ODs 20 fold with 342 ppm Ca++ water, mixing the dilutions and allowing them to stand for 24 hours and measuring the % creaming (Cr) and/or settlement (Set) after 30 minutes (30 min) and 24 hours (24 hr).

Application Example AEOD1

A screening test was run to see if the aqueous dispersant adversely affected the stabilisation provided by the structurants in the oil phases. The structurants were used at 5% in oil—a higher than normal structurant for an OD formulation but was used to highlight any adverse effect from the inclusion of dispersant. The oil, dispersant and structurant used in the test formulations together with the viscosity date are set out in Table AEOD1 below.

TABLE AEOD1

| | | | Clay1 | | Clay2 | |
|---|---|---|---|---|---|---|
| Ex No | Disp. | Oil | YS | Visc | YS | Visc |
| AEOD1.C1 | None | Oil1 | 5.2 | 800 | 5.2 | 850 |
| AEOD1.1 | SE1 | Oil1 | 3.9 | 630 | 0.8* | 95 |
| AEOD1.C2 | None | Oil2 | 3.9 | 1100 | 1.9 | 300 |
| AEOD1.2 | Se1 | Oil2 | 1.9 | 870 | 0.7 | 200 |

*Yield Stress not distinctly identified

The inclusion of dispersant results in a modest reduction in yield stress and viscosity when used with the clay structurants. These changes are as similar to those given on the inclusion of suitable non-ionic emulsifier surfactants and indicate that the compounds of the invention are compatible with these structurants for OD formulations.

Application Example AEOD2

An OD formulation containing agrochemical active was made up as follows:

| Material | weight % |
|---|---|
| Act4 | 20 |
| Clay1 | 3.5 |
| Surf1 | 17 |
| Surf2 | 0.5 |
| SE1 | 0.8 |
| Oil1 | to 100 |

The OD was tested for storage stability and dispersibility as described above and the results, indicating that the SE1 dispersant did not adversely affect the stability of the oil dispersion and retained its ability to disperse the solid active in water, are set out in Table AEOD2 below.

TABLE AEOD2

| | OD stability | | | | | | Dispersibility | | | |
|---|---|---|---|---|---|---|---|---|---|---|
| | Amb | | | 54° C. | | | Cr | | Set | |
| Ex no | 1 d | 1 w | 1 m | 1 d | 1 w | 1 m | 30 min | 24 hr | 30 min | 24 hr |
| AEOD2.1 | 0 | tr* | <5% | 0 | 50 | 80 | none | none | none | 4** |

*tr = trace of oil separation
**readily redispersed

What is claimed is:

1. A compound represented by formula (I):

$$[Hp]\text{-}[(Link1)\text{-}(OA)_n(Link2)R^1]_m \qquad (I)$$

wherein:

Hp represents a $C_{22}$-$C_{60}$ hydrocarbyl hydrophobe, comprising a hydrocarbyl residue of a polymerised fatty acid or an aralkylphenyl residue;

OA represents an oxyalkylene residue;

n represents a value in the range of 5-50;

m represents a value of 1-2, wherein the compound comprises a residue of a fatty acid dimer; or represents a value of 1-3, wherein the compound comprises a residue of a fatty acid trimer;

$R^1$ represents $-NR^2R^3$, $-(R^4)(R^5)N\rightarrow O$, $-(R^4)(R^5)N^+-R^6$, or $-(R^4)(R^5)N^+-R^7COO^-$;

$R^2$ and $R^3$ each independently represent hydrogen, $C_1$-$C_8$ alkyl, $C_2$-$C_8$ alkenyl, or together with the nitrogen atom forming a 5-7 membered heterocyclic ring optionally comprising one or more further heterocyclic atoms;

$R^4$ and $R^5$ each independently represent $C_1$-$C_8$ alkyl, $C_2$-$C_8$ alkenyl, or together with the nitrogen atom forming a 5-7 membered heterocyclic ring optionally comprising one or more further heterocyclic atoms;
$R^6$ represents $C_1$-$C_6$ alkyl;
$R^7$ represents $C_1$-$C_5$ alkylene;
Link1 represents a linking group comprising a direct bond, —CO—, —$OR^8C(O)$—, —$OC(O)R^9C(O)$—; or —OC(O)—;
$R^8$ represents a $C_1$-$C_4$ alkylene;
$R^9$ represents a $C_2$-$C_4$ alkylene;
Link2 represents a linking group comprising a direct bond, —$OCH_2CH(CH_3)$—, —$OCH_2CH(OH)CH_2$—, —$OC(O)R^{10}C(O)(X)(CH_2)_{n1}$—, or —$CH_2C(O)(X)(CH_2)_{n2}$—;
$R^{10}$ represents a $C_2$-$C_4$ alkylene;
X represents —O— or —NH—;
n1 represents a value in the range of 2-6; and
n2 represents a value in the range of 2-6.

2. The compound of claim 1, wherein the aralkylphenyl is a distyryl group, a tristyryl group, a dicumyl group, or a mixture including two or more of such groups.

3. The compound of claim 1, wherein oxyalkylene residue is an oxyethylene residue or an oxypropylene residue.

4. The compound of claim 1, wherein n represents a value in the range of 8-25.

5. The compound of claim 1, wherein n represents a value in the range of 10-15.

6. The compound of claim 1, wherein the compound is a surfactant compound.

7. The compound of claim 1, wherein the compound is a dispersing agent.

8. An aqueous dispersion, comprising:
 i) a solid active agrochemical; and
 ii) a dispersing agent, comprising one or more compounds of claim 1.

9. The aqueous dispersion of claim 8, wherein the dispersion is in the form of a dispersion concentrate.

10. The aqueous dispersion of claim 8, wherein the dispersion further comprises dissolved electrolyte.

11. The aqueous dispersion of claim 10, wherein the dissolved electrolyte is an agrochemical active.

12. The aqueous dispersion of claim 11, wherein the agrochemical active dissolved electrolyte is a water soluble herbicide or a water soluble fertiliser.

13. The aqueous dispersion of claim 8, wherein the dispersion is in the form of an agrochemical suspoemulsion, and said dispersion further comprising a liquid component emulsified in the aqueous continuous phase of said dispersion.

14. The aqueous dispersion of claim 8, wherein the dispersed active agrochemical is one or more plant growth regulators, herbicides, and/or pesticides.

15. A diluted formulation, comprising the dispersion of claim 8 in the form of a concentrate, diluted with water in an amount from 10 to 10,000 times the weight of the concentrate.

16. An agrochemical formulation, comprising:
 i) an active agrochemical; and
 ii) an adjuvant for the active agrochemical, said adjuvant comprising a compound of claim 1.

17. The agrochemical formulation of claim 16, wherein the formulation is in the form of an aqueous or oil based solution concentrate, an aqueous or oil based dispersion concentrate, an aqueous solution dispersion concentrate, or a suspoemulsion concentrate.

18. The agrochemical formulation of claim 16, wherein the active agrochemical comprises at least one plant growth regulator, herbicide, and/or pesticide.

19. The agrochemical formulation of claim 18, wherein the agrochemical active is a dissolved electrolyte.

20. A diluted formulation, comprising the formulation of claim 16 in the form of a concentrate, diluted with water in an amount from 10 to 10,000 times the weight of the concentrate.

21. An agrochemical formulation in the form of an oil dispersion concentrate, comprising:
 i) a water insoluble solid active agrochemical in a water immiscible non-aqueous liquid; and
 ii) one or more compounds of claim 1.

22. A diluted formulation, comprising the formulation of claim 21 in the form of a concentrate, diluted with water in an amount from 10 to 10,000 times the weight of the concentrate.

23. A composition, comprising one or more compounds represented by formula (I):

$$[Hp]-[(Link1)-(OA)_n(Link2)R^1]_m \qquad (I)$$

wherein:
Hp represents a $C_{22}$-$C_{60}$ hydrocarbyl hydrophobe, comprising a hydrocarbyl residue of a polymerised fatty acid or an aralkylphenyl residue;
OA represents an oxyalkylene residue;
n represents a value in the range of 5-50;
m represents a value of 1-2, wherein the compound comprises a residue of a fatty acid dimer; or represents a value of 1-3, wherein the compound comprises a residue of a fatty acid trimer;
$R^1$ represents —$NR^2R^3$, —$(R^4)(R^5)N\rightarrow O$, —$(R^4)(R^5)N^+$—$R^6$, or —$(R^4)(R^5)N^+$—$R^7COO_-$;
$R^2$ and $R^3$ each independently represent hydrogen, $C_1$-$C_8$ alkyl, $C_2$-$C_8$ alkenyl, or together with the nitrogen atom forming a 5-7 membered heterocyclic ring optionally comprising one or more further heterocyclic atoms;
$R^4$ and $R^5$ each independently represent $C_1$-$C_8$ alkyl, $C_2$-$C_8$ alkenyl, or together with the nitrogen atom forming a 5-7 membered heterocyclic ring optionally comprising one or more further heterocyclic atoms;
$R^6$ represents $C_1$-$C_6$ alkyl;
$R^7$ represents $C_1$-$0_5$ alkylene;
Link1 represents a linking group comprising a direct bond, —CO—, —$OR^8C(O)$—, —$OC(O)R^9C(O)$—; or —OC(O)—;
$R^8$ represents a $C_1$-$C_4$ alkylene;
$R^9$ represents a $C_2$-$C_4$ alkylene;
Link2 represents a linking group comprising a direct bond, —$OCH_2CH(CH_3)$—, —$OCH_2CH(OH)CH_2$—, —$OC(O)R^{10}C(O)(X)(CH_2)_{n1}$—, or —$CH_2C(O)(X)(CH_2)_{n2}$—;
$R^{10}$ represents a $C_2$-$C_4$ alkylene;
X represents —O— or —NH—;
n1 represents a value in the range of 2-6; and
n2 represents a value in the range of 2-6.

24. The composition of claim 23, wherein the aralkylphenyl is a distyryl group, a tristyryl group, a dicumyl group, or a mixture including two or more of such groups.

25. The composition of claim 23, wherein oxyalkylene residue is an oxyethylene residue or an oxypropylene residue.

26. The composition of claim 23, wherein n represents a value in the range of 8-25.

27. The composition of claim 23, wherein n represents a value in the range of 10-15.

28. The composition of claim 23, wherein at least one of the one or more compounds is a surfactant compound.

29. The composition of claim 23, wherein at least one of the one or more compounds is a dispersing agent.

30. The composition of claim 23, wherein at least one of the one or more compounds is an adjuvant.

31. An aqueous dispersion, comprising the composition of claim 23, wherein at least one of the one or more compounds is a dispersing agent.

32. The aqueous dispersion of claim 31, wherein the dispersion is in the form of a dispersion concentrate.

33. The aqueous dispersion of claim 31, wherein the dispersion is in the form of an agrochemical suspoemulsion, and said dispersion further comprising a liquid component emulsified in the aqueous continuous phase of said dispersion.

34. The aqueous dispersion of claim 31, wherein the dispersion further comprises dissolved electrolyte.

35. A diluted formulation, comprising the dispersion of claim 31 in the form of a concentrate, diluted with water in an amount from 10 to 10,000 times the weight of the concentrate.

36. An aqueous dispersion, comprising the composition of claim 23, wherein at least one of the one or more compounds is a dispersing agent.

37. An agrochemical composition, comprising:
   i) an active agrochemical; and
   ii) the composition of claim 23.

* * * * *